United States Patent [19]

Chambers

[11] 4,211,777

[45] Jul. 8, 1980

[54] COMPOSITIONS COMPRISING A COMPOUND HAVING SODIUM CROMOGLYCATE ACTIVITY AND AMINOSALICYLIC ACID

[75] Inventor: Albert Chambers, Loughborough, England

[73] Assignee: Fisons Limited, London, England

[21] Appl. No.: 906,974

[22] Filed: May 17, 1978

[30] Foreign Application Priority Data

Nov. 25, 1977 [GB] United Kingdom ............... 49105/77

[51] Int. Cl.² ........................................... A61K 31/625
[52] U.S. Cl. ................................................... 424/232
[58] Field of Search ............................... 424/232, 230

[56] References Cited

U.S. PATENT DOCUMENTS

| | | | |
|---|---|---|---|
| 2,977,281 | 3/1962 | Feier et al. | 424/230 |
| 3,039,925 | 6/1962 | Domagk et al. | 424/232 |
| 4,066,756 | 1/1978 | Orr et al. | 424/232 |

FOREIGN PATENT DOCUMENTS 1423985  2/1976  United Kingdom ..................... 424/283

OTHER PUBLICATIONS

*The Merck Index,* 9th Ed., 1976, Compound 491 & 492.

*Primary Examiner*—Frederick E. Waddell
*Attorney, Agent, or Firm*—Merriam, Marshall & Bicknell

[57] ABSTRACT

There is described a pharmaceutical composition comprising a compound having sodium cromoglycate like activity, as active ingredient, in combination with an aminosalicyclic acid or a pharmaceutically acceptable derivative thereof.

There are also described packages containing the separate components of the composition and pharmaceutical formulations containing the composition.

17 Claims, No Drawings

COMPOSITIONS COMPRISING A COMPOUND HAVING SODIUM CROMOGLYCATE ACTIVITY AND AMINOSALICYLIC ACID

This invention relates to a mixture and a method for its preparation.

Aminosalicylic acids and their pharmaceutically acceptable derivatives (hereinafter collectively called ASA), e.g. their salts and esters, have been used in mammals, mainly for the treatment of tuberculosis. However ASA suffers from the disadvantage of unwanted side effects. We have now surprisingly found that the side effects of ASA may be reduced by the use of certain disodium cromoglycate like compounds in combination with the ASA. The combinations are also more active in certain mammals than are their individual components and surprisingly are active in conditions in which ASA has not previously been used.

According to our invention therefore we provide a pharmaceutical composition comprising a compound having sodium cromoglycate like activity, as active ingredient, in combination with an ASA.

A compound having sodium cromoglycate like activity is able to inhibit the release of pharmacological mediators which result from the in vivo combination of certain types of antibody and specific antigen, for example the combination of reaginic antibody and specific antigen (see Example 27 of British Pat. No. 1,292,601—the rat passive cutaneous anaphylaxis test).

The active ingredients may be characterised by the following biological tests and results thereof.

The compound is first tested in the rat passive cutaneous anaphylaxis test. If the compound does not show significant inhibition of allergic manifestations at 20 mg/kg intraperitoneally (i.p) or intravenously (i.v) in this test, its activity is generally too low. Various other biological tests may be used to show that the compound exhibits its anti-allergy activity as an inhibitor of the release of mediators of anaphylaxis rather than as, for example an end organ antagonist or anti-cholinergic or adenyl cyclase stimulator. Therefore, tests to see if the compound antagonises the effect of histamine, serotonin, acetylcholine and slow reacting substance of anaphylaxis (SRSA), that is, that the compound is an end organ antagonist of the mediators, may be employed. Such tests are well known. Active ingredients according to the invention are not end organ antagonists.

Specific groups of active ingredients are to be found among the chromone-2-carboxylic acids, and suitable derivatives thereof, e.g. those described in British Pat. Nos. 1,368,243; 1,144,905; 1,230,087 and West German Pat. No. 2,553,688. Other active ingredients are to be found among the xanthones, e.g. of Belgian Pat. Nos. 759,292 and 787,843 and Dutch Pat. Nos. 72,09622 and 73,06958; among the compounds of Belgian Pat. No. 809,935; among the nitroindanediones, e.g. of Belgian Pat. No. 792,867; among the phenanthrolines, e.g. of Belgian Pat. No. 773,200; among the azapurines, e.g. of Belgian Pat. No. 776,683; the oxazoles, e.g. of West German OLS No. 2,459,380; the flavones, e.g of Belgian Pat. No. 823,875; and the oxamic acids, e.g. of West German Pat. No. 2,360,193 and of U.S. Pat. No. 4,038,398.

Particularly preferred are the chromones and chromone like compounds of British Pat. Nos. 1,144,905; and 1,230,087 and West German Pat. No. 2,553,688. More specifically we prefer 1,3-bis(2-carboxychromon-5-yloxy)propan-2-ol or a pharmaceutically acceptable derivative, e.g. salt such as the disodium salt, thereof; this latter is commonly known as sodium cromoglycate or cromolyn sodium. As further preferred compounds there may be mentioned 6,7,8,9-tetrahydro-4-oxo-10-propyl-4H-naphtho[2,3-b]pyran-2-carboxylic acid; 5-(2-hydroxypropoxy)-8-propyl-chromone-2-carboxylic acid; 6,7,8,9-tetrahydro-5-hydroxy-4-oxo-10-propyl-4H-naphtho[2,3-b]pyran-2-carboxylic acid and pharmaceutically acceptable derivatives of any one thereof.

Pharmaceutically acceptable derivatives of the above chromone-2-carboxylic acids include pharmaceutically acceptable salts, esters and amides of the 2-carboxylic acid group. Suitable salts include ammonium, alkali metal (e.g. sodium, potassium and lithium) salts and salts with suitable organic bases, e.g. salts with hydroxylamine, lower alkylamines such as methylamine or ethylamine, with substituted lower alkylamines, e.g. hydroxy substituted alkylamines such as tris(hydroxymethyl)methylamine, or with simple monocyclic nitrogen heterocyclic compounds, e.g. piperidine or morpholine. Suitable esters include simple lower alkyl esters, e.g. the ethyl ester, esters derived from alcohols containing basic groups, e.g. di-lower alkyl amino substituted alkanols such as the $\beta$-(diethylamino)-ethyl ester, and acyloxy alkyl esters, e.g. a lower acyloxy-lower alkyl ester such as the pivaloyloxymethyl ester, or a bis-ester derived from a dihydroxy compound, e.g. a di(hydroxy-lower alkyl) ether, e.g. the bis-2-oxapropan-1,3-diyl ester. The pharmaceutically acceptable salts of the basic esters, e.g. the hydrochloride, may also be used.

We prefer the composition to contain only one active ingredient.

From the group of compounds we call ASA we prefer to use 4-aminosalicyclic acid or 5-aminosalicyclic acid, or a pharmaceutically acceptable salt or ester of either thereof. Specific salts which may be mentioned include the sodium, potassium and calcium salts. A specific ester which may be mentioned is the phenyl ester.

The ratio of the ASA to the active ingredient will of course vary with the particular active ingredient, the particular ASA, the specific condition to be treated and with the particular patient. However for specific active ingredients we have found that the following ratios are appropriate, the parts by weight of the active ingredient being calculated as the sodium salt:

| ASA (parts by weight) | Active Ingredient (one part by weight) |
| --- | --- |
| (a) 0.8 to 35,000 preferably 1.6 to 20,000 more preferably 4 to 2,000 | 1,3-bis(2-carboxy chromon-5-yloxy) propan-2-ol or a pharmaceutically acceptable salt thereof |
| (b) 0.16 to 140 preferably 1.6 to 80 | 5-(2-hydroxypropoxy)-8-propyl-chromone-2-carboxylic acid, or a pharmaceutically acceptable salt thereof |
| (c) 2 to 7,000 preferably 8 to 4,000 | 6,7,8,9-tetrahydro-4-oxo-10-propyl-4H-naphtho[2,3-b]-pyran-2-carboxylic acid, or 6,7,8,9-tetrahydro-5-hydroxy-4-oxo-10-propyl-4H-naphtho[2,3-b]-pyran-2-carboxylic acid, or a pharmaceutically acceptable |

| ASA (parts by weight) | Active Ingredient (one part by weight) |
|---|---|
| | salt of either thereof |

The daily dosage of ASA (calculated as the free acid) for humans for most purposes is up to 5 g, preferably 0.4 to 3.5 g and more preferably 0.8 to 2.0 g. The ASA may be administered from 1 to 4 times per day.

Each dose of the ASA may comprise one or more unit doses, e.g. tablets or capsules.

The daily dosage of the active ingredient will naturally vary with the particular active ingredient. However for specific active ingredients we have found that the following daily dosages (calculated as the sodium salt) are appropriate:

| | |
|---|---|
| 1,3-bis(2-carboxy chromon-5-yloxy) propan-2-ol or a pharmaceutically acceptable salt thereof | up to 2g, preferably 0.5 to 1g and more preferably about 0.8g |
| 5-(2-hydroxypropoxy)-8-propyl-chromone-2-carboxylic acid, or a pharmaceutically acceptable salt thereof | 25mg to 10g, preferably 25 mg to 2g |
| 6,7,8,9-tetrahydro-4-oxo-10-propyl-4H-naphtho-[2,3-b]pyran-2-carboxylic acid, or 6,7,8,9-tetrahydro-5-hydroxy-4-oxo-10-propyl-4H-naphtho[2,3-b]-pyran-2-carboxylic acid, or a pharmaceutically acceptable salt of either thereof | 0.5mg to 800mg, preferably 0.5mg to 400mg |

For human use compositions in dosage form suitable for administration at one time, e.g. unit dosage form, comprise the quantities of active ingredient (calculated as the sodium salt), and of the ASA (calculated as the free acid) specified below:

(a) ASA

Up to 5 g, preferably 0.1 to 3.5 g and more preferably 0.2 to 2.0 g.

(b) 1,3-Bis-(2-carboxychromon-5-yloxy)propan-2-ol 0.1 to 500 mg, preferably 1 to 200 mg and more preferably 1 to 50 mg. We particularly prefer compositions in unit dosage form comprising up to 100 mg, as higher unit doses may tend to cause an increase in gastrointestinal irritation.

(c)
5-(2-Hydroxypropoxy)-8-propyl-chromone-2-carboxylic acid 25 mg to 2.5 g, preferably 25 to 500 mg.

(d)
6,7,8,9-Tetrahydro-4-oxo-10-propyl-4H-naphtho[2,3-b]pyran-2-carboxylic acid or
6,7,8,9-Tetrahydro-5-hydroxy-4-oxo-10-propyl-4H-naphtho[2,3-b]pyran-2-carboxylic acid 0.5 to 200 mg, preferably 0.5 to 100 mg.

Specific conditions which may be beneficially treated with the compositions of the invention include Crohn's disease, atrophic gastritis, ulcerative colitis, proctitis, distal proctocolitis, stump proctitis, coeliac disease, regional ileitis, peptic ulceration, gastrointestinal allergy and irritable bowel syndrome.

According to our invention we also provide a method for the treatment of a condition of the gastrointestinal tract, which comprises administration of a composition according to the invention to an individual mammal, e.g. human, suffering from such a condition. The administration is preferably administration by mouth (oesophagael administration) or via the rectum.

According to the invention we also provide a method for the treatment of a condition for the gastrointestinal tract, which comprises sequential or simultaneous administration of active ingredient and an ASA to an individual mammal, e.g. human, suffering from such a condition or disorder.

The active ingredient is preferably administered in such a way that it is available in the gastrointestinal tract, e.g. the colon, at the same time as the ASA. Alternatively the active ingredient may be administered before or after the ASA.

When sequential or simultaneous administration of active ingredient and the ASA is used the ratios and dosages are as described above with respect to the mixtures.

The invention therefore also provides a pharmaceutical package comprising at least one dose of active ingredient and at least one dose of an ASA. The doses are preferably unit doses and are preferably arranged in the package in a particular order together with written or printed indications or directions, the indications or directions and the manner of packing being such as to provide guidance in relation to and to facilitate the taking of a unit dose of active ingredient and a unit dose of the ASA in a particular order or combination, e.g. a unit dose of the former at the same time as a unit dose of the latter. The package is preferably a sealed package and may comprise a tube, box or chart in or on which the unit doses are packed. The unit doses are preferably suitable for oesophagaeal administration and preferably contain the doses of active ingredient and the ASA in the ratios set out above for the combinations.

In order to produce suitable compositions the active ingredient and the ASA, either separately or as a mixture thereof, are worked up with organic or inorganic pharmaceutically acceptable adjuvants or excipients. Examples of such adjuvants are:

For tablets and dragees: Binders, for example, cellulosic materials, e.g. microcrystalline cellulose and methyl cellulose; disintegrating agents, for example starches, e.g. maize starch; stabilizers, e.g. against hydrolysis of the active ingredients; flavouring agents, for example sugars such as lactose; fillers; stearates and inorganic diluents, e.g. talc.

For syrups, suspensions or dispersions: A liquid vehicle in which the active ingredients may be dissolved or suspended, e.g. water; and suspending agents, e.g. cellulose derivatives, gums etc.

For hard or soft capsules: Diluents, e.g. lactose; glidants, e.g. stearates; inorganic materials, e.g. silica or talc; stabilizers and dispersing agents.

For suppositories: Natural or hardened oils, waxes etc. A large number of proprietary emulsifying bases are available and are suitable for use in suppositories. These include 'Witepsol' bases, consisting of hydrogenated triglycerides of lauric acid with added monoglycerides; and 'Massupol' bases, which consist of glyceryl esters of lauric acid with a very small amount of glycerol monostearate.

For enemas: Water, sodium chloride, buffers, etc.

We prefer compositions which are designed to be administered by mouth (oesophageally) or as enemas, e.g. retention enemas.

The composition may also contain further adjuvants, for example a composition for use in tablets may contain lubricants and glidants to assist in tabletting, e.g. magnesium stearate, or wetting agents to assist in granulation, e.g. dioctyl sodium sulphosuccinate. The composition may also if desired contain a pharmaceutically acceptable dye or colourant, and may, if desired, be coated using conventional film or sugar coating techniques.

If desired the composition, or one or more components thereof, may be formulated in sustained or controlled release form, e.g. by coating some or all of the drug particles themselves or granules thereof made with, for example, sucrose and of a size up to 2 mm in diameter with a layer of, e.g. beeswax, Carnuba wax, stearic or palmitic acids, cetyl alcohol or similar substances which could be expected to be slowly dissolved or digested or to act as semi-permeable membranes through which the drugs can diffuse when the preparations are ingested. The compositions may contain drug particles or granules which are uncoated in admixture with particles or granules having one or more coats of the coating medium, and may be in the form of a capsule containing the particles or granules or alternatively a tablet, for which other adjuvants may be required, such as glidants or lubricants. The mixture may be administered as an enteric coated composition to make the drugs available at the appropriate part of the gastrointestinal tract. This may be achieved by coating the tablet with a continuous film of material which is resistant and impermeable to gastric secretions, but which is susceptible to intestinal secretions. Typical film materials are shellac and its derivatives and cellulose acetate phthalate.

The active ingredient and the ASA may, if desired, be used in a specific form, e.g. having a mass median diameter of less than 10 microns.

The active ingredient and the ASA may also be formulated as an aqueous, e.g. a water chloroform (400:1), solution containing from 0.001 to 10.0% by weight of the total content of the active ingredient and the ASA.

We prefer compositions containing disodium cromoglycate.

The compositions desirable contain from 0.1 to 85% by weight of the or each active ingredient present, and more desirably from 0.1 to 10% by weight thereof.

I claim:

1. A pharmaceutical composition suitable for oesophageal or rectal administration comprising one part by weight of 1,3-bis(2-carboxychromon-5-yloxy)propan-2-ol or a pharmaceutically acceptable salt thereof, as active ingredient, in combination with 0.8 to 35,000 parts of an aminosalicylic acid or a pharmaceutically acceptable salt or ester thereof.

2. A composition in accordance with claim 1, wherein said active ingredient is sodium cromoglycate.

3. A composition in accordance with claim 1 comprising 1.6 to 20,000 parts of said aminosalicylic acid, or salt or ester thereof.

4. A composition in accordance with claim 1 comprising 4 to 2,000 parts of said aminosalicylic acid, or salt or ester thereof.

5. A composition according to claim 1 comprising from 0.1 to 500 mg of 1,3-bis(2-carboxychromon-5-yloxy)propan-2-ol, or a pharmaceutically acceptable salt thereof, calculated as the sodium salt, in a form suitable for administration at one time.

6. A composition according to claim 5 comprising from 1 to 200 mg of 1,3-bis(2-carboxychromon-5-yloxy)propan-2-ol, or a pharmaceutically acceptable salt thereof, calculated as the sodium salt.

7. A composition according to claim 6 comprising from 1 to 50 mg of 1,3-bis(2-carboxychromon-5-yloxy)-propan-2-ol, or a pharmaceutically acceptable salt thereof, calculated as the sodium salt.

8. A pharmaceutical composition suitable for oesophageal or rectal administration comprising one part by weight of 5-(2-hydroxypropoxy)-8-propyl-chromone-2-carboxylic acid or a pharmaceutically acceptable salt thereof, as active ingredient, in combination with 0.16 to 140 parts of an aminosalicylic acid or a pharmaceutically acceptable salt or ester thereof.

9. A composition in accordance with claim 8 comprising 1.6 to 80 parts of said aminosalicylic acid, or salt or ester thereof.

10. A pharmaceutical composition suitable for oesophageal or rectal administration comprising one part by weight of 6,7,8,9-tetrahydro-4-oxo-10-propyl-4-H-naphtho[2,3-b]-pyran-2-carboxylic acid or 6,7,8,9-tetrahydro-5-hydroxy-4-oxo-10-propyl-4H-naphtho[2,3-b]-pyran-2-carboxylic acid, or a pharmaceutically acceptable salt thereof, as active ingredient, in combination with 2 to 7,000 parts of an aminosalicylic acid or a pharmaceutically acceptable salt or ester thereof.

11. A composition in accordance with claim 10 comprising 8 to 4,000 parts of said aminosalicylic acid, or salt or ester thereof.

12. A composition in accordance with any one of claims 1, 8, or 10, wherein said aminosalicylic acid is 4-aminosalicylic acid or 5-aminosalicylic acid.

13. A composition in accordance with claim 12 comprising from 0.1 to 3.5 g. of said aminosalicylic acid or salt or ester thereof, in a form suitable for administration at one time.

14. A composition in accordance with claim 12 comprising from 0.2 to 2.0 g of said aminosalicylic acid or salt or ester thereof, in a form suitable for administration at one time.

15. A composition in accordance with claim 12 in a form adapted to be administered oesophageally.

16. A composition in accordance with claim 12 in the form of a suppository or enema.

17. A composition in accordance with claim 12, wherein said composition, or one or more of the components thereof, is formulated in sustained release form.

* * * * *